(12) United States Patent
Kang et al.

(10) Patent No.: US 10,360,319 B2
(45) Date of Patent: Jul. 23, 2019

(54) PARTICLE-BASED MODELING METHOD AND APPARATUS

(71) Applicant: Samsung Electronics Co., Ltd., Suwon-si (KR)

(72) Inventors: Nahyup Kang, Seoul (KR); Hyong Euk Lee, Suwon-si (KR); Ji Yeon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1089 days.

(21) Appl. No.: 14/515,747

(22) Filed: Oct. 16, 2014

(65) Prior Publication Data

US 2015/0120258 A1    Apr. 30, 2015

(30) Foreign Application Priority Data

Oct. 28, 2013  (KR) .................. 10-2013-0128642

(51) Int. Cl.
  *G06F 17/50*    (2006.01)
  *G16H 50/50*    (2018.01)
  *G06F 19/00*    (2018.01)

(52) U.S. Cl.
  CPC .......... *G06F 17/5009* (2013.01); *G06F 19/00* (2013.01); *G16H 50/50* (2018.01); *G06F 2217/16* (2013.01)

(58) Field of Classification Search
  None
  See application file for complete search history.

(56) References Cited

U.S. PATENT DOCUMENTS

| 2006/0159621 | A1  | 7/2006  | Barrett |
| 2007/0239414 | A1* | 10/2007 | Song ................... G06F 17/5018 703/9 |
| 2011/0321181 | A1  | 12/2011 | Shimura et al. |
| 2012/0203530 | A1  | 8/2012  | Sharma et al. |
| 2012/0215510 | A1  | 8/2012  | Metaxas |
| 2013/0070062 | A1* | 3/2013  | Fouras ............... H04N 13/0203 348/50 |

(Continued)

FOREIGN PATENT DOCUMENTS

| JP | 2011-206155    | 10/2011 |
| KR | 10-2006-0114878 | 11/2006 |
| KR | 10-2007-0053750 | 5/2007  |

(Continued)

OTHER PUBLICATIONS

Markus Becker et al., "Weakly compressible SPH for free surface flows", Eurographics/ACM SIGGRAPH Symposium on Computer Animation, 2007, 9 pages.

(Continued)

*Primary Examiner* — Craig C Dorais
(74) *Attorney, Agent, or Firm* — NSIP Law

(57) ABSTRACT

A particle-based modeling method and apparatus may include searching for a second particle neighboring a first particle in a vector field at a current time, and updating a position of each of the first particle and the second particle in each vector field over time, based on correcting a velocity of each of the first particle and the second particle based on a variation satisfying an incompressible constraint condition for each of the first particle and the second particle.

30 Claims, 10 Drawing Sheets

(56) References Cited

U.S. PATENT DOCUMENTS

2014/0149055 A1* 5/2014 Falahatpisheh ......... G01P 5/001
                                                                    702/45

FOREIGN PATENT DOCUMENTS

| KR | 10-2009-0029849 | 3/2009 |
|----|-----------------|--------|
| KR | 10-2011-0069980 | 6/2011 |
| KR | 10-2011-0103178 | 9/2011 |
| KR | 10-1094793 | 12/2011 |
| WO | 2011/029996 A1 | 3/2011 |

OTHER PUBLICATIONS

B. Solenthaler et al., "Predictive-Corrective Incompressible SPH", ACM Transactions on Graphics, vol. 28, No. 3, Article 40, Aug. 2009, 6 pages.
Miles Macklin et al., "Position Based Fluids", ACM TOG 32(4), Jul. 2013, 5 pages.
Sharen J. Cummins et al., "An SPH Projection Method", Journal of Computational Physics 152, 1999, 24 pages.
Hagit Schechter et al., "Ghost SPH for Animating Water", ACM Trans. Graph. 31, 4, Jul. 2012, 8 pages.

* cited by examiner

FIG. 4

Algorithm 1 Simulation Loop

1: for each particle $i$ do
2:    find neighboring particles $N_i$
3: end for
4: for each particle $i$ do
5:    update density
6:    $\rho_i = \sum_{j \in N_i} m_j W(x_i - x_j, h)$
7: end for
8: for each particle $i$ do
9:    apply external forces (eg. gravity)
10:    $u_i = u_i + \Delta t f_{ext}(x_i)$
11: end for
12: for each particle $i$ do
13:    smooth velocity
14:    $u_i = u_i + \sum_{j \in N_i} \frac{m_j}{\rho_j}(u_j - u_i) W(x_i - x_j, h)$
15: end for
16: while iter<maxIters and $\nabla \cdot u_i$ >threshold do
17:    for each particle $i$ do
18:      update divergence
19:      $\nabla \cdot u_i = \sum_{j \in N_i} \frac{m_j}{\rho_j}(u_j - u_i) \cdot W(x_i - x_j, h)$
20:    end for
21:    for each particle $i$ do
22:      project velocity
23:      $u_i += \Delta u_i$
24:    end for
25: end while
26: for each particle $i$ do
27:    update position
28:    $x_i = x_i + \Delta t u_i$
29: end for
30: apply constant density constraint (optional)

PARTICLE-BASED MODELING METHOD AND APPARATUS

CROSS-REFERENCE TO RELATED APPLICATIONS

This application claims the priority benefit of Korean Patent Application No. 10-2013-0128642, filed on Oct. 28, 2013, in the Korean Intellectual Property Office, the disclosure of which is incorporated herein by reference.

BACKGROUND

1. Field

Example embodiments of the following description relate to a particle-based modeling method and apparatus.

2. Description of the Related Art

Navier-Stokes equations define a fluid to be a sum of extremely small particles, and describe how particles move while interacting with each other. For example, when an ideal situation is assumed, the Navier-Stokes equations may be changed to a Bernoulli's principle that is simpler than the Navier-Stokes equations. The ideal situation may include, for example, a situation that remains unchanged over time, and in which an incompressible fluid is provided and moves by only an influence on a gravity field without friction. To realistically reproduce fluid modeling based on the Navier-Stokes equations, an incompressible condition may be required to be satisfied.

Because typical particle-based methods assume compressibility as a basic concept, it may be difficult to satisfy an incompressible condition in the Navier-Stokes equations. To satisfy the incompressible condition, a large-scale linear system, that is, a pressure-Poisson equation may be used. However, an efficiency of the pressure-Poisson equation may be reduced due to heavy computation in a linear system.

SUMMARY

In fluid modeling, such as realistically illustrating water flow in a pipe, or simulating blood flow in an artery, for example, a fluid may be represented with many (e.g. tens of thousands) small particles. Because particle positions are calculated based on a relationship with neighboring particles, near a boundary surface, such as a pipe or artery wall, for example, where fewer neighboring particles exist, the fluid modeling may be less efficient, less stable, and less accurate. For example, particles may be artificially generated on the boundary surface that generate a repulsive force, resulting in a less accurate model near the boundary surface. Furthermore, solving a pressure Poisson equation may involve heavy computation requirements.

Accordingly, fluid modeling without solving a pressure Poisson equation may increase processing efficiency. Also, virtual particles may be generated outside the boundary surface, and the mass and density of the virtual particles may be adjustable. By using neighboring virtual particles outside the boundary surface, in addition to the neighboring particles inside the boundary surface, particles near the boundary surface may be more accurately modeled.

The foregoing and/or other aspects are achieved by providing a particle-based modeling method including searching for a second particle neighboring a first particle in a vector field at a current time, computing a variation satisfying an incompressible constraint condition, for each of the first particle and the second particle, correcting a velocity of each of the first particle and the second particle, based on the variation, and updating a position of each of the first particle and the second particle in each vector field over time, based on the corrected velocity.

The incompressible constraint condition may satisfy the following equation:

$$C_i(u_i) = \nabla \cdot u_i$$

Here, $u_i$ denotes a velocity of a particle i, $C_i(u_i)$ denotes an incompressible constraint condition for the particle i, and $\nabla \cdot u_i$ denotes a divergence of the velocity $u_i$.

The computing may include computing the variation, based on a correction value that is used to correct a velocity error of each of the first particle and the second particle in the vector field at the current time.

The correction value may satisfy the following equation:

$$\lambda = -\frac{C_i(u_i)}{|\nabla u_i C_i(u_i)|^2}$$

Here, $\lambda$ denotes a correction value, $C_i(u_i)$ denotes an incompressible constraint condition for a velocity of the particle i, and $\nabla u_i$ denotes a del of the velocity of the particle i.

The computing may include iteratively computing the variation until the variation converges to a predetermined threshold.

The particle-based modeling method may further include initializing information including at least one of a mass, a velocity, and a position of each of particles including the first particle and the second particle.

The particle-based modeling method may further include calculating a momentum conservation equation for each of the first particle and the second particle.

The calculating may include calculating at least one of a density, an external force, and a smooth viscosity of each of the first particle and the second particle.

The particle-based modeling method may further include applying a boundary condition to each of the first particle and the second particle.

The applying may include applying the boundary condition to each of the first particle and the second particle in the updated position.

The applying may include anisotropically arranging the first particle and the second particle, extracting a boundary surface of a space including the first particle and the second particle, separating particles located adjacent to the boundary surface from among the particles including the first particle and the second particle, casting rays from the separated particles to the boundary surface, and generating virtual particles, the virtual particles being disposed point symmetrically with respect to the separated particles, generating particles neighboring the separated particles, based on the virtual particles, and calculating a momentum conservation equation for each of the separated particles and the neighboring particles, and applying the boundary condition.

The applying may include generating virtual particles used to maintain a density of each of the first particle and the second particle in a boundary surface of a space including the first particle and the second particle.

The generating may include generating virtual particles used to maintain a density of each of the first particle and the second particle, by adjusting a mass of each of the virtual particles or a number of the virtual particles in the boundary surface.

The first particle and the second particle may include particles included in a three-dimensional (3D) blood vessel-shaped model based on information on a blood vessel area.

The particle-based modeling method may further include analyzing a blood flow in a blood vessel, based on the boundary condition and the 3D blood vessel-shaped model, transforming the 3D blood vessel-shaped model, based on a result of the analyzing, and regenerating a blood vessel, using the transformed 3D blood vessel-shaped model.

The first particle and the second particle may include particles forming at least one object of computer graphics.

The foregoing and/or other aspects are achieved by providing a particle-based modeling apparatus including a search unit to search for a second particle neighboring a first particle in a vector field at a current time, a variation computing unit to compute a variation satisfying an incompressible constraint condition, for each of the first particle and the second particle, a correcting unit to correct a velocity of each of the first particle and the second particle, based on the variation, and a position updating unit to update a position of each of the first particle and the second particle in each vector field over time, based on the corrected velocity.

The variation computing unit may compute the variation, based on a correction value that is used to correct a velocity error of each of the first particle and the second particle in the vector field at the current time.

The variation computing unit may iteratively compute the variation until the variation converges to a predetermined threshold.

The particle-based modeling apparatus may further include an initializing unit to initialize information including at least one of a mass, a velocity, and a position of each of particles including the first particle and the second particle.

The particle-based modeling apparatus may further include a calculating unit to calculate a momentum conservation equation for each of the first particle and the second particle.

The calculating unit may calculate at least one of a density, an external force, and a smooth viscosity of each of the first particle and the second particle.

The particle-based modeling apparatus may further include an applying unit to apply a boundary condition to each of the first particle and the second particle.

The applying unit may include a boundary surface extractor to anisotropically arrange the first particle and the second particle, and to extract a boundary surface of a space including the first particle and the second particle, a virtual particle generator to separate particles located adjacent to the boundary surface from among the particles including the first particle and the second particle, to cast rays from the separated particles to the boundary surface, and to generate virtual particles, the virtual particles being disposed point symmetrically with respect to the separated particles, and a boundary condition applier to generate particles neighboring the separated particles, based on the virtual particles, to calculate a momentum conservation equation for each of the separated particles and the neighboring particles, and to apply the boundary condition.

The applying unit may include a generator to generate virtual particles used to maintain a density of each of the first particle and the second particle in the boundary surface of the space including the first particle and the second particle.

The generator may generate virtual particles used to maintain a density of each of the first particle and the second particle, by adjusting a mass of each of the virtual particles or a number of the virtual particles in the boundary surface.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 4 illustrates a diagram of an algorithm to perform a particle-based modeling method according to example embodiments;

DETAILED DESCRIPTION

Figure 1:
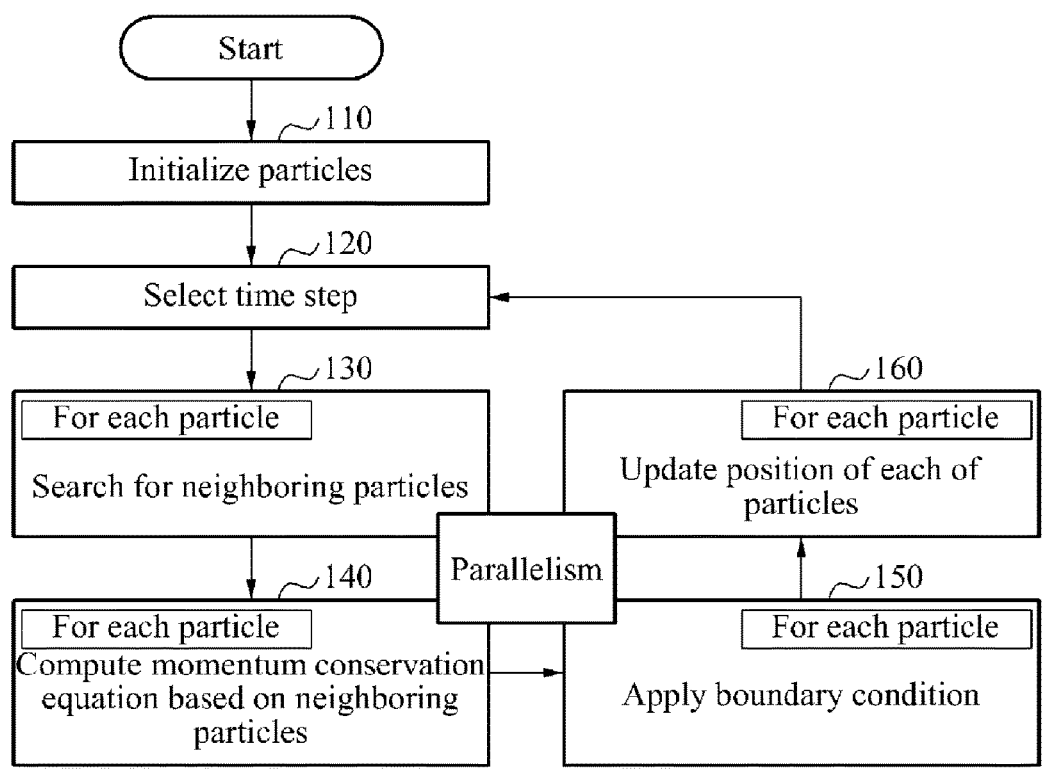
FIG. 1 illustrates a flowchart of a process of performing a particle-based modeling method according to example embodiments.

Reference will now be made in detail to embodiments, examples of which are illustrated in the accompanying drawings, wherein like reference numerals refer to like elements throughout. Example embodiments are described below to explain the present disclosure by referring to the figures.

FIG. 1 illustrates a flowchart of a process of performing a particle-based modeling method according to example embodiments.

Referring to FIG. 1, in operation 110, a modeling apparatus according to example embodiments may initialize particles used to perform modeling of a fluid. For example, in operation 110, the modeling apparatus may initialize information regarding a mass, a density, or a position of each of particles representing a fluid in a predetermined space or a predetermined area.

In operation 120, the modeling apparatus may select a time step. For example, when a single period of modeling is assumed to be 1 second (s), the modeling apparatus may perform modeling of motions of particles gradually, for example, every 0.5 s or 0.3 s, instead of modeling of the motions at once for 1 s, so that a motion of a single particle, and motions of neighboring particles may be sufficiently reflected. Operation 120 may indicate determining a number of time steps into which a single period is divided, for example 0.5 s or 0.3 s. The time step may be selected appropriately by the modeling apparatus or a user of the modeling apparatus.

In operation 130, the modeling apparatus may search for a second particle neighboring a first particle in a vector field at a current time. In the present disclosure, at least one first particle, or a plurality of first particles may be provided, and at least one second particle, or a plurality of second particles may be provided.

In operation 140, the modeling apparatus may compute a momentum conservation equation for the first particle, based on the neighboring second particle. For example, in operation 140, the modeling apparatus may further calculate a momentum conservation equation for a density, an external force, a smooth viscosity, and the like of the first particle, based on the second particle.

The modeling apparatus may compute a variation satisfying an incompressible constraint condition for the first particle, based on a result obtained by computing the momentum conservation equation. A scheme of computing the variation satisfying the incompressible constraint condition will be described based on Equations 1 to 6 below.

In operation 140, the modeling apparatus may iteratively compute the variation until the variation converges to a predetermined threshold.

In operation 150, the modeling apparatus may apply a boundary condition to each of the first particle and the second particle. In operation 150, the modeling apparatus may use the momentum conservation equation computed in operation 140 in various boundary conditions.

A boundary condition may be represented, for example, by porosity modeling between the first particle and the second particle, by a solid boundary condition for the first particle and the second particle, by modeling of a mass sink by the first particle and the second particle, and the like. In the porosity modeling, a probabilistic model may be used. In operation 150, the modeling apparatus may infer a boundary of an area including the first particle and the second particle, through an anisotropic field.

In operation 160, the modeling apparatus may correct a velocity of each of the first particle and the second particle, based on the variation computed in operation 140, and may update a position of each of the first particle and the second particle in each vector field over time, based on the corrected velocity.

Subsequently, the modeling apparatus may perform operations 130 through 160 on all particles in a predetermined area. Operations 130 through 160 may be iteratively and in parallel performed on all particles in a vector field.

As described above, because in typical particle-based methods, compressibility of a fluid is assumed as a basic concept, it may be difficult to satisfy an incompressible condition in the Navier-Stokes equations. The compressibility may be defined as a property enabling a volume or density of a fluid to be changed based on a pressure, and incompressibility may be defined as a property enabling a volume or density of a fluid to remain almost unchanged based on a pressure.

To satisfy an incompressible condition without a solving process for the pressure Poisson equation, a smoothed-particle hydrodynamics (SPH) scheme may be used. The SPH scheme is known to those skilled in the art and accordingly, further description thereof is omitted herein.

A divergence for a velocity of a particle i in a vector field, based on the SPH scheme, may be represented by Equation 1 below.

$$\nabla \cdot u_i = \sum_{j \in N} \frac{m_j}{\rho_j}(u_j - u_i) \cdot \nabla W(x_{ij})$$ [Equation 1]

In Equation 1, i denotes a particle included in a vector field, j denotes a particle neighboring the particle i. Additionally, N denotes a number of particles included in the vector field and is a natural number.

Additionally, $m_j$ a denotes a mass of the particle j, and $\rho_j$ denotes a density of the particle j. $u_j$ denotes a velocity of the particle j, and $u_i$ denotes a velocity of the particle i. $\Delta W$ denotes a weighting function, or a kernel function, and $x_{ij}$ denotes a distance between the particles i and j, that is, indicates $x_i - x_j$. In the present disclosure, a velocity of a particle may refer to a flow velocity of a particle in a vector field.

$\nabla W(x_{ij})$ may be identical to $\nabla W(x_i - x_j, h)$, and h denoting a smoothing length may refer to a spatial distance between particles.

An incompressible constraint condition C for the particle i in Equation 1 may be represented by Equation 2 below.

$$C_u(u_i) = \nabla \cdot u_i$$ [Equation 2]

In Equation 2, $C_i(u_i)$ denotes an incompressible constraint condition for a velocity of the particle i, and $\nabla \cdot u_i$ denotes a divergence of the velocity of the particle i.

For example, when a divergence of the velocity of the particle i is zero, the incompressible constraint condition may be satisfied. Additionally, to obtain, in real time, a variation $\Delta u_i$ of the particle i that satisfies the incompressible constraint condition, Equation 2 may be represented in the form of an approximate value, using a Taylor series, as shown in Equation 3 below.

$$C_i(u_i + \Delta u_i) \approx C_i(u_i) \nabla u_i C_i(u_i) \cdot \Delta u_i = 0$$

The variation $\Delta u_i$ may be quickly minimized, when a motion direction of the particle i is matched to a direction of a gradient, and accordingly Equation 3 may be represented as shown in Equation 4 below.

$$\Delta u_i = \lambda \nabla u_i C_i(u_i)$$ [Equation 4]

In Equation 4, $\nabla u_i$ denotes del of the velocity of the particle i.

In Equation 4, $\lambda$ denotes a correction value used to correct a velocity error of each of the first particle and the second particles, in the vector field at the current time, and may be represented by Equation 5 below.

$$\lambda = -\frac{C_i(u_i)}{|\nabla u_i C_i(u_i)|^2}$$ [Equation 5]

When Equation 5 is substituted into Equation 4, the variation $\Delta u_i$ may be represented as shown in Equation 6 below.

$$\Delta u_i = -\frac{C_i(u_i)}{|\nabla u_i C_i(u_i)|^2} \nabla u_i C_i(u_i)$$ [Equation 6]

According to example embodiments, a velocity of each of particles may be corrected by calculation of the variation $\Delta u_i$, so that a divergence of a vector field of each of the particles may be zero. Accordingly, an incompressible condition may be satisfied, without a solving process for the pressure Poisson equation.

According to example embodiments, the modeling apparatus may facilitate parallelism, or multi-threading, and may reproduce a fluid phenomenon or a fluid movement in real time, by using a particle-based modeling method. Therefore, it is possible to perform realistic fluid modeling in a game field or a mobile user interface (UI) field in which realtime is considered to be important, as well as, in special effects of movies that require realistically reproducing of images with high-quality.

Figure 2:
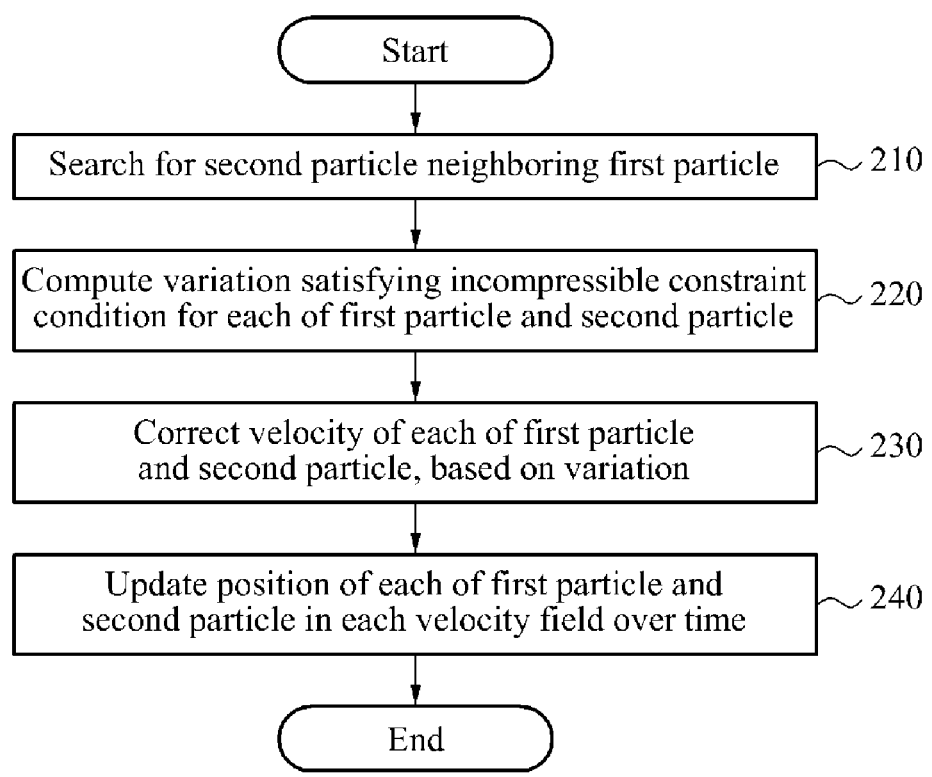
FIG. 2 illustrates a flowchart of an example of a particle-based modeling method according to example embodiments.

FIG. 2 illustrates a flowchart of an example of a particle-based modeling method according to example embodiments.

Referring to FIG. 2, in operation 210, a modeling apparatus according to example embodiments may search for a second particle neighboring a first particle in a vector field.

In operation 220, the modeling apparatus may compute a variation satisfying an incompressible constraint condition, for each of the first particle and the second particle. The incompressible constraint condition may satisfy Equation 2 that is described above. A scheme of computing a variation of a particle that satisfies a condition of Equation 2 has been described above with reference to FIG. 1 and accordingly, further description thereof is omitted herein.

In operation 230, the modeling apparatus may correct a velocity of each of the first particle and the second particle, based on the variation.

In operation 240, the modeling apparatus may update a position of each of the first particle and the second particle in each vector field over time, based on the velocity of each of the first particle and the second particle corrected in 230.

Figure 3:
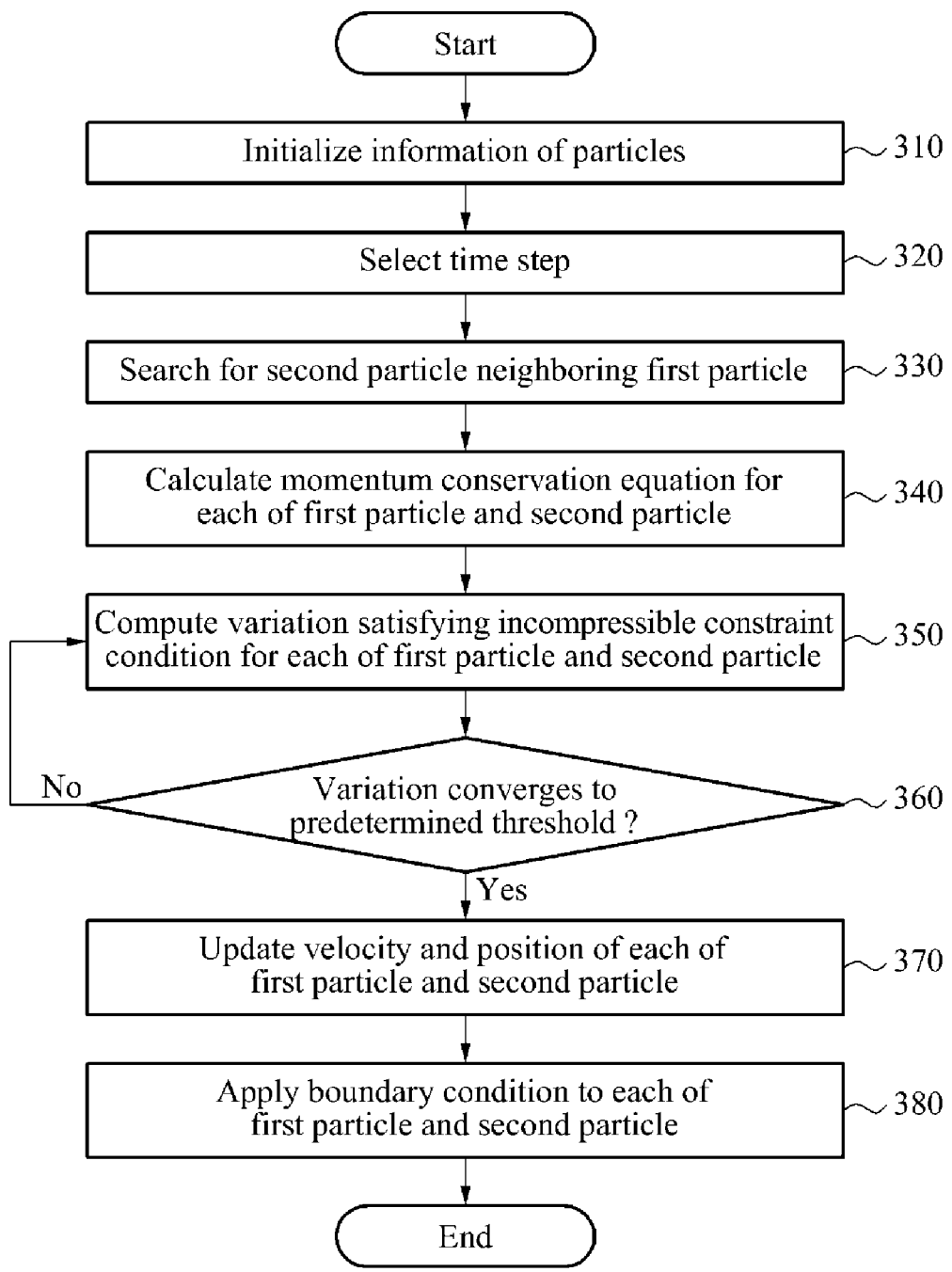
FIG. 3 illustrates a flowchart of another example of a particle-based modeling method according to example embodiments.

FIG. 3 illustrates a flowchart of another example of a particle-based modeling method according to example embodiments, and FIG. 4 illustrates a diagram of an algorithm to perform a particle-based modeling method according to example embodiments.

Referring to FIG. 3, in operation 310, a modeling apparatus according to example embodiments may initialize information of particles. The particles may include, for example, a first particle, and a second particle neighboring the first particle. The information of the particles may include, for example, a mass, a velocity, a position, and the like of each of the particles. Additionally, at least one second particle may be provided.

In operation 310, the modeling apparatus may initialize information regarding a mass, a velocity, a position, and the like of each of the first particle and the second particle. For example, the first particle may represent a fluid in a predetermined space or a predetermined area.

In operation 320, the modeling apparatus may select a time step, for example, a time step $\Delta t$ of FIG. 4. For example, in 320, the modeling apparatus may select a time in which modeling of motions of particles is to be performed.

In operation 330, the modeling apparatus may search for the second particle in a vector field at a current time. Operation 330 may be expressed as coded in lines 1 to 3 of the algorithm of FIG. 4.

In operation 340, the modeling apparatus may calculate a momentum conservation equation for each of the first particle and the second particle. For example, in operation 340, the modeling apparatus may calculate a momentum conservation equation for the first particle, based on the second particle. In this example, the modeling apparatus may calculate a density, an external force, a smooth viscosity, and the like of each of the particles including the first particle and the second particle.

For example, the modeling apparatus may calculate a density $\rho_i$ of each of the particles, based on an equation "$\rho_i = \Sigma_{j \in N} m_j W(x_i - x_j, h)$" coded in a line 6 of FIG. 4.

The modeling apparatus may calculate an external force of each of the particles, based on an equation "$u_i = u_i + \Delta t f_{ext}(x_i)$" coded in a line 10 of FIG. 4.

The modeling apparatus may calculate a smooth viscosity of each of the particles, based on an equation $$"u_i = u_i + \sum_{j \in N} \frac{m_j}{\rho_j}(u_j - u_i)W(x_i - x_j, h)"$$

coded in a line 14 of FIG. 4.

In operation 350, the modeling apparatus may compute a variation satisfying an incompressible constraint condition for each of the first particle and the second particle, based on a result obtained by calculating the momentum conservation equation in operation 340. In operation 350, the modeling apparatus may acquire a divergence in a vector field of each of the particles, based on an equation $$"\nabla \cdot u_i = \sum_{j \in N} \frac{m_j}{\rho_j}(u_j - u_i) \cdot W(x_i - x_j, h)"$$

coded in a line 19 of FIG. 4, and may set the divergence to zero, to satisfy the incompressible constraint condition.

In operation 360, the modeling apparatus may determine whether the variation computed in operation 350 converges to a predetermined threshold. In operation 360, the modeling apparatus may enable a divergence for a flow velocity of the particle i to converge to the predetermined threshold, as shown in $\nabla \cdot u_i >$threshold, so that an incompressible condition may be satisfied. The threshold may be set in advance to a value closest to zero, for example, 0.01, or 0.0001, based on a performance of a system.

When the variation is determined not to converge to the predetermined threshold in operation 360, the modeling apparatus may recompute the variation satisfying the incompressible constraint condition, for each of the first particle and the second particle in operation 350. A maximum number of iterations, denoted by maxIters in a line 16 of FIG. 4, may be set in advance, based on a number of particles, and the like.

When the variation is determined to converge to the predetermined threshold in operation 360, the modeling apparatus may update a velocity and a position of each of the first particle and the second particle in operation 370.

Operations 350 through 370 may be expressed as coded in lines 16 through 29 of FIG. 4.

In operation 380, the modeling apparatus may apply a boundary condition to each of the first particle and the second particle.

An order of operations 310 through 380 performed by the modeling apparatus is not limited to an order of FIG. 3 and accordingly, operations 330 through 380 may be performed in parallel, or in orders other than the order of FIG. 3.

According to example embodiments, the modeling apparatus may also be implemented to use a density-invariant SPH method, together with the particle-based modeling method. The density-invariant SPH method may satisfy a density invariant condition, to satisfy an incompressible condition.

In the density-invariant SPH method, accuracy of modeling may be reduced, because an incompressible condition is not directly dealt with. However, a stable solution may be continuously acquired. Accordingly, by using both the two methods, accuracy of modeling may be enhanced. The density-invariant SPH method is known to those skilled in the art and accordingly, further description thereof is omitted herein.

Figure 5:
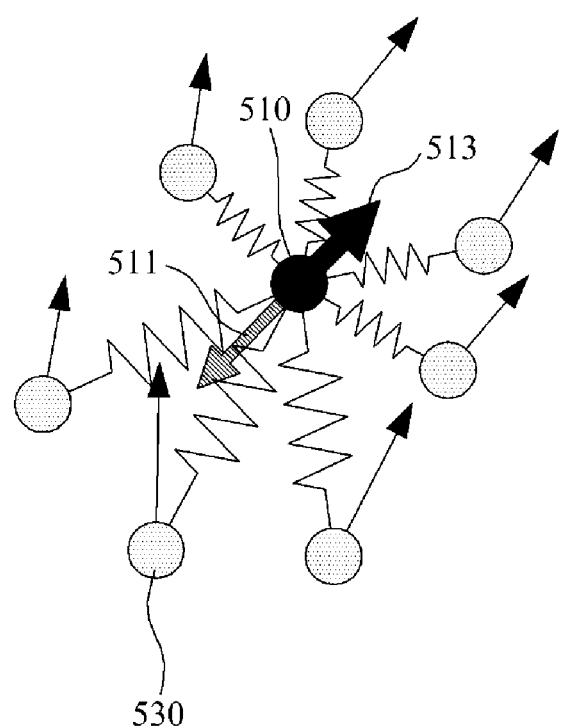
FIG. 5 illustrates a diagram of an incompressible constraint condition used in a particle-based modeling method according to example embodiments.

FIG. 5 illustrates a diagram of an incompressible constraint condition used in a particle-based modeling method according to example embodiments.

FIG. 5 illustrates a great difference between a vector field caused by attractive force and repulsive force generated based on only a position distribution between a target particle that is to calculate an incompressible velocity and neighboring particles, and an incompressible velocity that reflects a velocity of each of neighboring particles.

Referring to FIG. 5, particle-based modeling may be performed, by correcting a velocity of each of particles, so that an incompressible constraint condition of a vector field may be satisfied.

The incompressible constraint condition may refer to an invariant condition of an internal volume of a fluid. The incompressible constraint condition may be used to control an output amount between particles based on a velocity of each of the particles in a predetermined vector field, and to enable high-accuracy modeling of a boundary surface by an interaction between a fluid and a solid.

As described above with reference to Equation 5, a correction value used to correct a velocity error of each of the first particle and the second particle in the vector field at the current time may be a setting value or a correction value used to satisfy an incompressible constraint condition for each of particles. The correction value may be calculated in parallel and iteratively.

In FIG. 5, an arrow 511 pointing in a lower-left direction from a fluid particle 510 indicates a result obtained by calculating a velocity when a distance between fluid particles is maintained. An arrow 513 pointing in an upper-right direction indicates a result obtained by computing an optimum velocity for conservation of a volume of a fluid, based on both a velocity difference and a position relationship between the fluid particle 510 and neighboring particles. Additionally, each of lines extending from the fluid particle 510 indicates a fluid velocity of a neighboring fluid particle 530 that is connected to the fluid particle 510.

Figure 6:
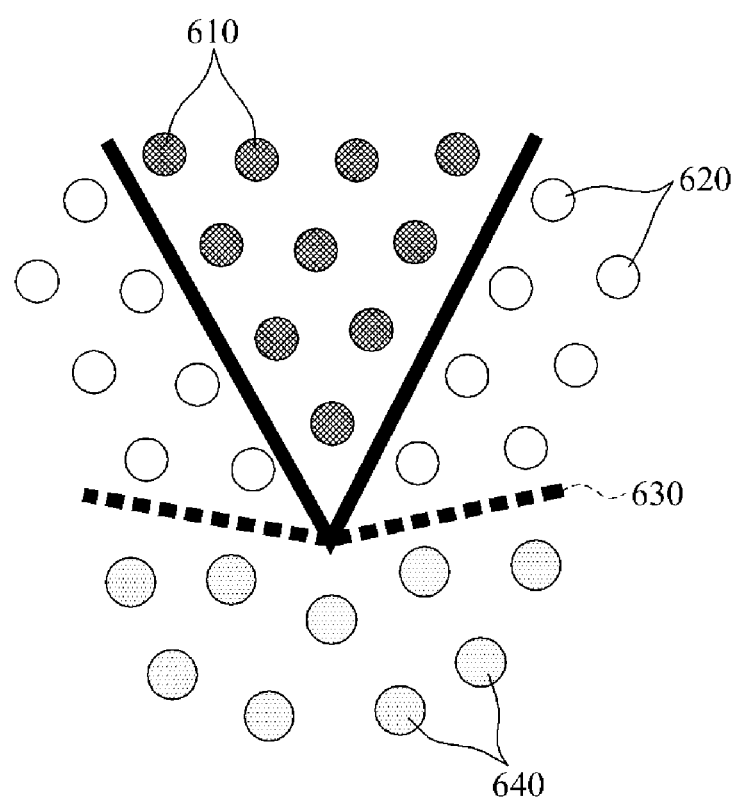
FIG. 6 illustrates a diagram of a scheme of applying a boundary condition by adjusting a density of virtual particles in a particle-based modeling method according to example embodiments.

FIG. 6 illustrates a diagram of a scheme of applying a boundary condition by adjusting a density of virtual particles in a particle-based modeling method according to example embodiments.

Referring to FIG. 6, a modeling apparatus according to example embodiments may adjust a density of a virtual particle within a predetermined vector field, and may represent a complex, high-accuracy boundary surface.

The modeling apparatus may generate virtual particles 620 that maintain the same density as fluid particles 610 included in a vector field, in a boundary surface 630 of a fluid. The modeling apparatus may adjust a number of virtual particles 640 in a vector field, or a mass of the virtual particles 640, using a scheme of adding or adjusting the virtual particles 640, so that a density of each of particles may be identical to a density of a fluid.

The boundary surface 630 between the fluid and a solid may be modeled in the form of a piecewise polygon.

Figure 7:
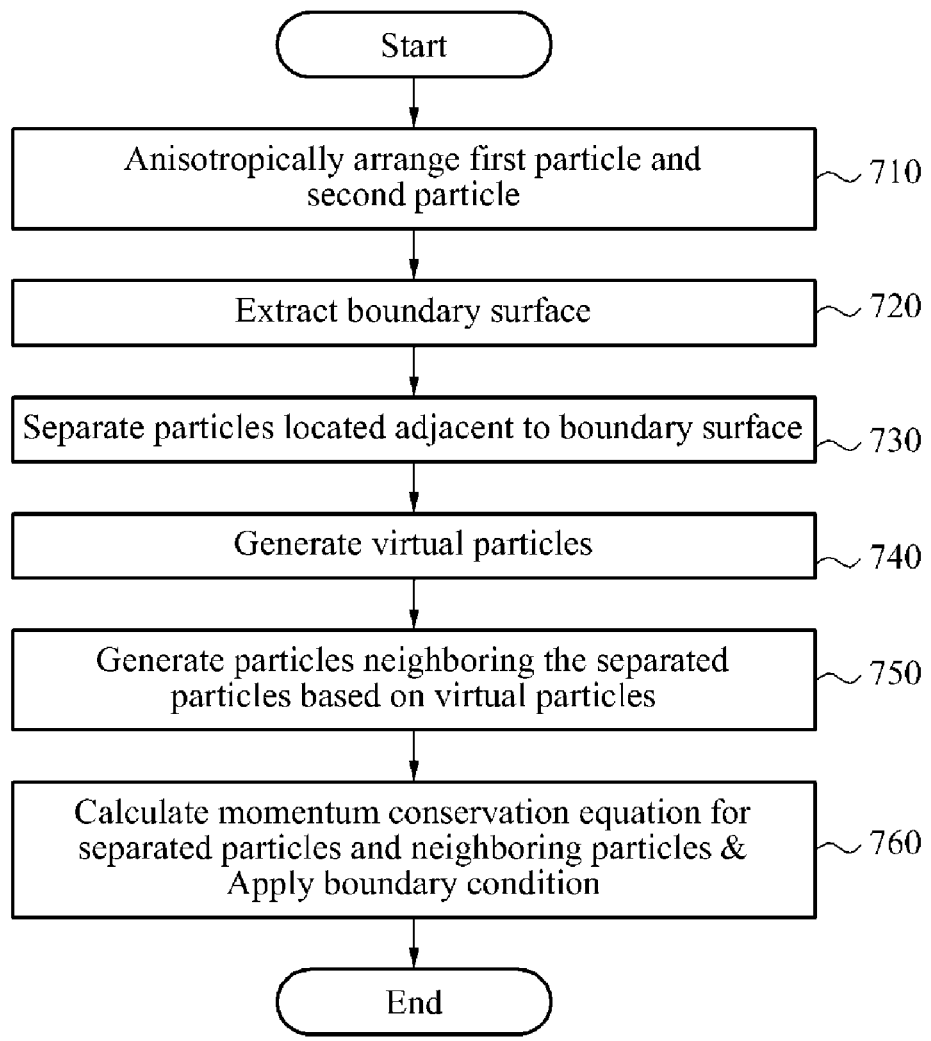
FIG. 7 illustrates a flowchart of a scheme of applying a boundary condition in a particle-based modeling method according to example embodiments.

FIG. 7 illustrates a flowchart of a scheme of applying a boundary condition in a particle-based modeling method according to example embodiments.

Referring to FIG. 7, a modeling apparatus according to example embodiments may perform modeling of motions of particles that are located in a boundary surface or located adjacent to the boundary surface, as if the particles move. In operation 710, the modeling apparatus may anisotropically arrange a first particle and a second particle in a predetermined area or a predetermined space. For example, in operation 710, the modeling apparatus may evenly arrange particles in an anisotropic scalar field.

In operation 720, the modeling apparatus may extract a boundary surface of a space including the first particle and the second particle.

In operation 730, the modeling apparatus may separate particles located adjacent to the boundary surface from among particles including the first particle and the second particle.

In operation 740, the modeling apparatus may cast rays from the separated particles to the boundary surface, and may generate virtual particles that are disposed point symmetrically with respect to the separated particles. An operation in which the modeling apparatus generates virtual particles that are disposed point symmetrically with respect to a single particle will be described with reference to FIG. 8 below.

In operation 750, the modeling apparatus may generate particles neighboring the particles separated in operation 730, based on the virtual particles.

In operation 760, the modeling apparatus may calculate a momentum conservation equation for the particles separated in operation 730 and the particles generated in operation 750, and may apply a boundary condition to the particles.

Figure 8:
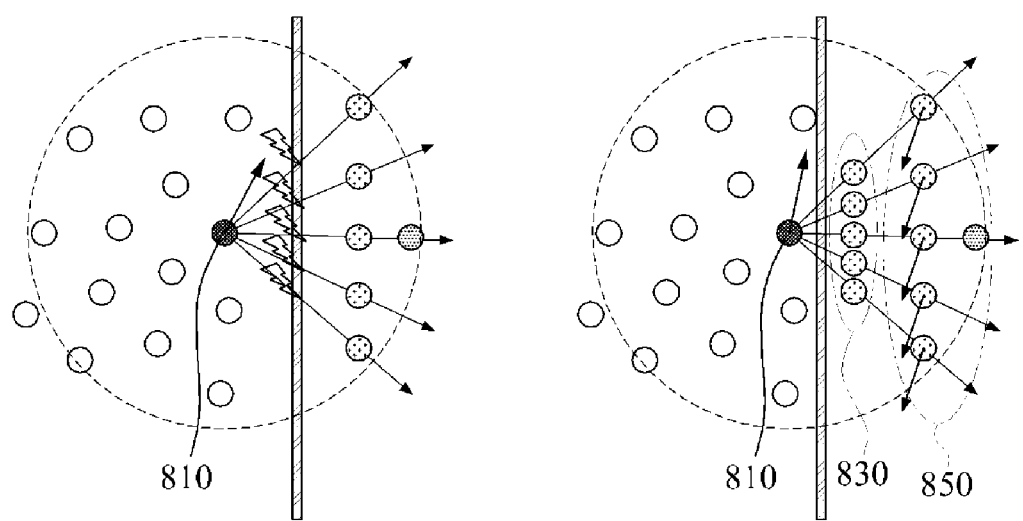
FIG. 8 illustrates a diagram of a scheme of applying a solid boundary condition as a boundary condition, in a particle-based modeling method according to example embodiments.

FIG. 8 illustrates a diagram of a scheme of applying a solid boundary condition as a boundary condition, in a particle-based modeling method according to example embodiments.

A boundary may be formed between an external environment and a space or an area that includes a fluid, such as water or blood, for example, by a solid wall, such as a water pipe or a blood vessel, for example.

Particle-based modeling basically requires a sufficient number of neighboring particles located around a single particle. However, because particles are insulated from surroundings by a solid wall in a boundary surface, it may be difficult to arrange neighboring particles enough to perform particle-based modeling. Additionally, a particle located in the boundary surface may be modeled differently from a real particle.

Accordingly, a particle-based modeling method for naturally representing motions of particles by applying various boundary conditions to particles located in the boundary surface may be provided.

Referring to FIG. 8, rays may be casted from a particle of interest 810 located adjacent to a boundary surface to the boundary surface, and virtual particles 830 may be generated. The virtual particles 830 may be disposed point symmetrically with respect to the interest particle 810. For example, when the particle of interest 810 is assumed to be a first particle, a modeling apparatus may cast rays from the first particle 810 to the boundary surface, and may generate the virtual particles 830 disposed point symmetrically with respect to the first particle 810. In this example, an arrow of the particle of interest 810 may indicate a current velocity of the particle of interest 810. Five radial arrows extending from the interest particle 810 may indicate virtual rays that are casted radially to recognize a boundary surface of an obstacle. The modeling apparatus may generate second particles 850 neighboring the first particle 810, using the virtual particles 830. Arrows of the virtual particles 830 may indicate velocities obtained by plane symmetry for the current velocity of the particle of interest 810. Accordingly, based on a distance, shape, and/or or complexity between the boundary surface and the particle of interest 810, a number of rays used to generate the virtual particles 830 may be incremented by at least "1."

By calculating a momentum conservation equation for the first particle 810 and the second particles 850, a motion of a particle located adjacent to the boundary surface may be realistically represented. At least one virtual particle 830 and at least one second particle 850 may be generated.

According to example embodiments, a first particle and a second particle may include particles included in a three-dimensional (3D) blood vessel-shaped model based on information regarding a blood vessel area. A modeling apparatus according to example embodiments may analyze a blood flow in a blood vessel, based on the 3D blood vessel-shaped model and the above-described boundary condition, may transform the 3D blood vessel-shaped model based on a result of the analyzing, and may regenerate a blood vessel.

The first particle and the second particle may include, for example, particles forming at least one object of computer graphics. The modeling apparatus may analyze flowing of a fluid in a predetermined vector field, for example a river, oil, and the like, based on the above-described boundary condition and a 3D shaped model that is implemented by computer graphics, and may represent a flow of a stereoscopic object, for example, a fluid such as a river water, based on a result of the analyzing.

As described above, a particle-based modeling method according to example embodiments may be used to express a flow of a fluid, for example, water or other liquids, in a game field or a mobile UI field, or used to express a flow of a fluid, for example a blood flow, in a medial image.

Figure 9:
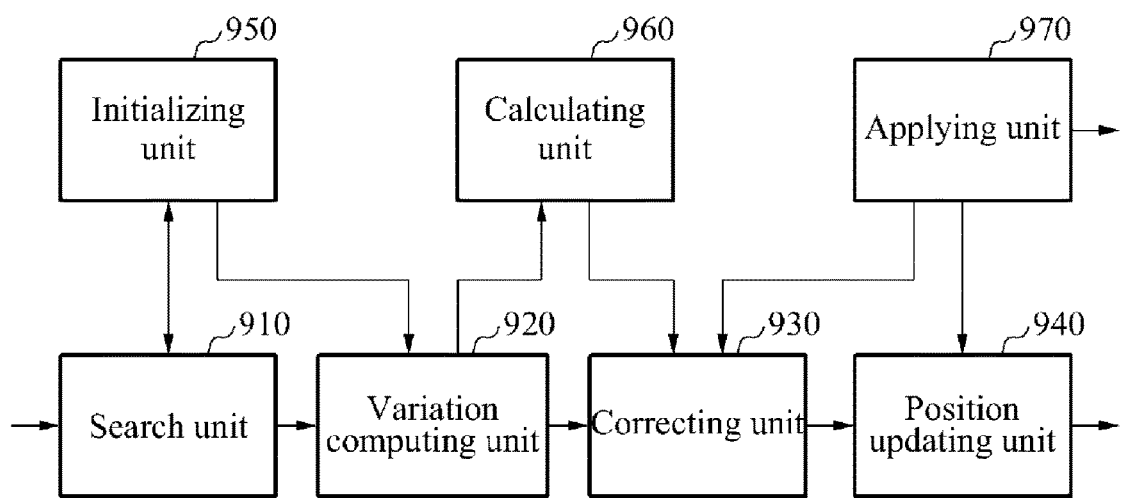
FIG. 9 illustrates a block diagram of a particle-based modeling apparatus according to example embodiments.

FIG. 9 illustrates a block diagram of a particle-based modeling apparatus according to example embodiments.

Referring to FIG. 9, a modeling apparatus 900 may include a search unit 910, a variation computing unit 920, a correcting unit 930, a position updating unit 940, an initializing unit 950, a calculating unit 960, and an applying unit 970.

The search unit 910 may search for a second particle neighboring a first particle in a vector field at a current time.

The variation computing unit 920 may compute a variation satisfying an incompressible constraint condition, for each of the first particle and the second particle. The incompressible constraint condition may satisfy Equation 2 that is described above. A scheme of computing a variation of a particle that satisfies a condition of Equation 2 has been described above with reference to FIG. 1 and accordingly, further description thereof is omitted herein.

The variation computing unit 920 may compute a variation $\Delta u_i$, based on a correction value $\lambda$ that is used to correct a velocity error of each of the first particle and the second particle in the vector field at the current time. The correction value $\lambda$ may be obtained using Equation 5 that is described above, and the variation $\Delta u_i$ may be expressed as shown in Equation 6 that is described above.

The variation computing unit 920 may iteratively compute the variation until the variation converges to a predetermined threshold.

The correcting unit 930 may correct a velocity of each of the first particle and the second particle, based on the variation computed by the variation computing unit 920.

The position updating unit 940 may update a position of each of the first particle and the second particle, in each vector field over time, based on the velocity corrected by the correcting unit 930.

The initializing unit 950 may initialize information including at least one of a mass, a velocity, and a position of each of particles including the first particle and the second particle.

The calculating unit 960 may calculate a momentum conservation equation for each of the first particle and the second particle. The calculating unit 960 may calculate at least one of a density, an external force, and a smooth viscosity of each of the first particle and the second particle.

The applying unit 970 may apply a boundary condition to each of the first particle and the second particle. The boundary condition may include, for example, porosity modeling between the first particle and the second particle, a solid boundary condition for the first particle and the second particle, modeling of a mass sink by the first particle and the second particle, and the like. Hereinafter, a configuration of the applying unit 970 will be further described with reference to FIG. 10.

Figure 10:
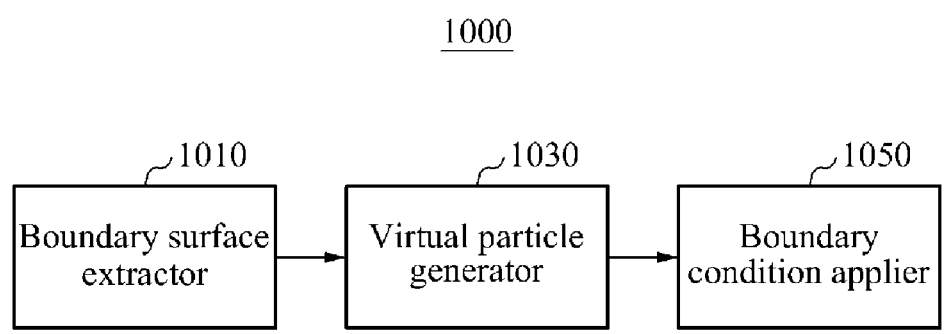
FIG. 10 illustrates a block diagram of an applying unit in a particle-based modeling apparatus according to example embodiments.

FIG. 10 illustrates a block diagram of an applying unit in a particle-based modeling apparatus according to example embodiments.

Referring to FIG. 10, the applying unit 1000 may include a boundary surface extractor 1010, a virtual particle generator 1030, and a boundary condition applier 1050.

The boundary surface extractor 1010 may anisotropically arrange a first particle and a second particle, and may extract a boundary surface of a space including the first particle and the second particle.

The virtual particle generator 1030 may separate particles located adjacent to the boundary surface from among particles including the first particle and the second particle, may cast rays from the separated particles to the boundary surface, and may generate virtual particles. The virtual particles may be disposed point symmetrically with respect to the separated particles.

The boundary condition applier 1050 may generate particles neighboring the separated particles, based on the virtual particles generated by the virtual particle generator 1030, may calculate a momentum conservation equation for the separated particles and the neighboring particles, and may apply the boundary condition to the particles.

Additionally, the applying unit 1000 may further include a generator (not shown).

The generator may generate virtual particles used to maintain a density of each of the first particle and the second particle in the boundary surface of the space including the first particle and the second particle. For example, the generator may generate the virtual particles, by adjusting a mass of each of the virtual particles or a number of the virtual particles in the boundary surface.

The units described herein may be implemented using hardware components and software components. For example, the hardware components may include microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device. Examples of the non-transitory computer readable recording medium include read-only memory (ROM), random-access memory (RAM), CD-ROMs, magnetic tapes, floppy disks, optical data storage devices. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

As a non-exhaustive illustration only, a terminal or device described herein may refer to mobile devices such as a cellular phone, a personal digital assistant (PDA), a digital camera, a portable game console, and an MP3 player, a portable/personal multimedia player (PMP), a handheld e-book, a portable laptop PC, a global positioning system (GPS) navigation, a tablet, a sensor, and devices such as a desktop PC, a high definition television (HDTV), an optical disc player, a setup box, a home appliance, and the like that are capable of wireless communication or network communication consistent with that which is disclosed herein.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A particle-based method performed by a particle-based modeling apparatus comprising a processor, the method comprising:
   searching, by the processor, for a second particle neighboring a first particle in a vector field at a current time;
   computing, by the processor, a variation satisfying an incompressible constraint condition, for each of the first particle and the second particle;
   correcting, by the processor, a velocity of each of the first particle and the second particle, based on the variation; and
   determining, by the processor, a position of each of the first particle and the second particle in each vector field over time, based on the corrected velocity,
   wherein the processor computes a correction value that is used to correct a velocity error of each of the first particle and the second particle in the vector field at the current time, and
   wherein the processor uses the correction value to satisfy the incompressible constraint condition of the first particle and the second particle.

2. The particle-based modeling method of claim 1, wherein the incompressible constraint condition satisfies the following equation:

$$C_i(u_i) = \nabla \cdot u_i$$

wherein $u_i$ denotes a velocity of a particle i, $C_i(u_i)$ denotes an incompressible constraint condition for the particle i, and $\nabla \cdot u_i$ denotes a divergence of the velocity $u_i$.

3. The particle-based modeling method of claim 1, wherein the computing, by the processor, comprises computing the variation, based on the correction value that is used to correct the velocity error of each of the first particle and the second particle in the vector field at the current time.

4. The particle-based modeling method of claim 3, wherein the correction value satisfies the following equation:

$$\lambda = -\frac{C_i(u_i)}{|\nabla u_i C_i(u_i)|^2}$$

wherein $\lambda$ denotes a correction value, $C_i(u_i)$ denotes an incompressible constraint condition for a velocity of the particle i, and $\nabla u_i$ denotes a del of the velocity of the particle i.

5. The particle-based modeling method of claim 1, wherein the computing, by the processor, comprises iteratively computing the variation until the variation converges to a predetermined threshold.

6. The particle-based modeling method of claim 1, further comprising:
   initializing, by the processor, information comprising at least one of a mass, a velocity, and a position of each of particles comprising the first particle and the second particle.

7. The particle-based modeling method of claim 1, further comprising:
   calculating, by the processor, a momentum conservation equation for each of the first particle and the second particle.

8. The particle-based modeling method of claim 7, wherein the calculating, by the processor, comprises calculating at least one of a density, an external force, and a smooth viscosity of each of the first particle and the second particle.

9. The particle-based modeling method of claim 1, further comprising:
   applying, by the processor, a boundary condition to each of the first particle and the second particle.

10. The particle-based modeling method of claim 9, wherein the applying, by the processor, comprises applying the boundary condition to each of the first particle and the second particle in the updated position.

11. The particle-based modeling method of claim 9, wherein the applying comprises:
  anisotropically arranging, by the processor, the first particle and the second particle;
  extracting, by the processor, a boundary surface of a space comprising the first particle and the second particle;
  separating, by the processor, particles located adjacent to the boundary surface from among the particles comprising the first particle and the second particle;
  casting, by the processor, rays from the separated particles to the boundary surface, and generating virtual particles, the virtual particles being disposed point symmetrically with respect to the separated particles;
  generating, by the processor, particles neighboring the separated particles, based on the virtual particles; and
  calculating a momentum conservation equation for each of the separated particles and the neighboring particles, and applying the boundary condition.

12. The particle-based modeling method of claim 9, wherein the applying, by the processor, comprises generating virtual particles used to maintain a density of each of the first particle and the second particle in a boundary surface of the space comprising the first particle and the second particle.

13. The particle-based modeling method of claim 12, wherein the generating, by the processor, comprises generating virtual particles used to maintain a density of each of the first particle and the second particle, by adjusting at least one of a mass of each of the virtual particles and a number of the virtual particles in the boundary surface.

14. The particle-based modeling method of claim 9, wherein the first particle and the second particle comprise particles included in a three-dimensional (3D) blood vessel-shaped model based on information on a blood vessel area.

15. The particle-based modeling method of claim 14, further comprising:
  analyzing, by the processor, a blood flow in a blood vessel, based on the boundary condition and the 3D blood vessel-shaped model;
  transforming, by the processor, the 3D blood vessel-shaped model, based on a result of the analyzing; and
  regenerating, by the processor, the blood vessel, using the transformed 3D blood vessel-shaped model.

16. The particle-based modeling method of claim 9, wherein the first particle and the second particle comprise particles forming at least one object of computer graphics.

17. A non-transitory computer readable recording medium storing a program to cause a computer to implement the particle-based modeling method of claim 1.

18. A particle-based modeling apparatus, comprising:
  a processor configured to
    search for a second particle neighboring a first particle in a vector field at a current time;
    compute a variation satisfying an incompressible constraint condition, for each of the first particle and the second particle;
    correct a velocity of each of the first particle and the second particle, based on the variation; and
    determine a position of each of the first particle and the second particle in each vector field over time, based on the corrected velocity,
  wherein the processor is further configured to compute a correction value that is used to correct a velocity error of each of the first particle and the second particle in the vector field at the current time, and
  wherein the processor uses the correction value to satisfy the incompressible constraint condition of the first particle and the second particle.

19. The particle-based modeling apparatus of claim 18, wherein the processor is further configured to compute the variation, based on the correction value that is used to correct the velocity error of each of the first particle and the second particle in the vector field at the current time.

20. The particle-based modeling apparatus of claim 18, wherein the processor is further configured to iteratively compute the variation until the variation converges to a predetermined threshold.

21. The particle-based modeling apparatus of claim 18, wherein the processor is further configured to initialize information comprising at least one of a mass, a velocity, and a position of each of particles comprising the first particle and the second particle.

22. The particle-based modeling apparatus of claim 18 wherein the processor is further configured to calculate a momentum conservation equation for each of the first particle and the second particle.

23. The particle-based modeling apparatus of claim 22, wherein the processor is further configured to calculate at least one of a density, an external force, and a smooth viscosity of each of the first particle and the second particle.

24. The particle-based modeling apparatus of claim 18 wherein the processor is further configured to apply a boundary condition to each of the first particle and the second particle.

25. The particle-based modeling apparatus of claim 24, wherein the processor is further configured to:
  anisotropically arrange the first particle and the second particle, and to extract a boundary surface of a space comprising the first particle and the second particle;
  separate particles located adjacent to the boundary surface from among the particles comprising the first particle and the second particle, to cast rays from the separated particles to the boundary surface, and to generate virtual particles, the virtual particles being disposed point symmetrically with respect to the separated particles; and
  generate particles neighboring the separated particles, based on the virtual particles, to calculate a momentum conservation equation for each of the separated particles and the neighboring particles, and to apply the boundary condition.

26. The particle-based modeling apparatus of claim 24 wherein the processor is further configured to generate virtual particles used to maintain a density of each of the first particle and the second particle in the boundary surface of the space comprising the first particle and the second particle.

27. The particle-based modeling apparatus of claim 26, wherein the processor is further configured to generate virtual particles used to maintain a density of each of the first particle and the second particle, by adjusting at least one of a mass of each of the virtual particles and a number of the virtual particles in the boundary surface.

28. The particle-based modeling apparatus of claim 18, wherein the incompressible constraint condition refers to at least one of a volume or a density of a fluid to remain almost unchanged based on a pressure.

29. A particle-based modeling method performed by a particle-based modeling apparatus comprising a processor, the method comprising:

evaluating, by the processor, a momentum conservation equation for a first particle based on a neighboring second particle;

determining, by the processor, a variation satisfying an incompressible constraint condition for the first particle based on the momentum conservation equation; and determining, by the processor, a velocity and a position of the first particle and the second particle based on the variation, wherein the processor determines the variation based on a correction value that is used to correct a velocity error of each of the first particle and the second particle in a vector field at a current time.

30. A non-transitory computer-readable recording medium storing a program to implement the method of claim 29.

* * * * *